United States Patent
Takayama et al.

(10) Patent No.: US 12,222,351 B2
(45) Date of Patent: Feb. 11, 2025

(54) IMMUNOASSAY AND MEASUREMENT REAGENT FOR LEUCINE-RICH ALPHA2 GLYCOPROTEIN

(71) Applicants: SEKISUI MEDICAL CO., LTD., Tokyo (JP); NATIONAL INSTITUTES OF BIOMEDICAL INNOVATION, HEALTH AND NUTRITION, Ibaraki (JP)

(72) Inventors: Shigeo Takayama, Tokyo (JP); Tetsuji Naka, Ibaraki (JP); Satoshi Serada, Ibaraki (JP)

(73) Assignees: SEKISUI MEDICAL CO., LTD., Tokyo (JP); NATIONAL INSTITUTES OF BIOMEDICAL INNOVATION, HEALTH AND NUTRITION, Ibaraki (JP)

( * ) Notice: Subject to any disclaimer, the term of this patent is extended or adjusted under 35 U.S.C. 154(b) by 960 days.

(21) Appl. No.: 17/282,307

(22) PCT Filed: Oct. 8, 2019

(86) PCT No.: PCT/JP2019/039564
§ 371 (c)(1),
(2) Date: Apr. 1, 2021

(87) PCT Pub. No.: WO2020/075691
PCT Pub. Date: Apr. 16, 2020

(65) Prior Publication Data
US 2021/0382041 A1    Dec. 9, 2021

(30) Foreign Application Priority Data

Oct. 9, 2018  (JP) ................................. 2018-190905

(51) Int. Cl.
*G01N 33/545* (2006.01)

(52) U.S. Cl.
CPC ....... *G01N 33/545* (2013.01); *G01N 2400/00* (2013.01)

(58) Field of Classification Search
None
See application file for complete search history.

(56) References Cited

U.S. PATENT DOCUMENTS

| | | | |
|---|---|---|---|
| 2007/0184503 A1 | 8/2007 | Jemmerson | |
| 2010/0190662 A1* | 7/2010 | Sutphen | G01N 33/57449 435/7.1 |
| 2011/0195438 A1 | 8/2011 | Kondou et al. | |
| 2014/0080143 A1 | 3/2014 | Takahashi et al. | |
| 2014/0113387 A1 | 4/2014 | Matsumoto et al. | |
| 2014/0377881 A1* | 12/2014 | Kitahara | C08F 212/08 436/501 |

FOREIGN PATENT DOCUMENTS

| | | | |
|---|---|---|---|
| AU | 2010274320 A1 | 1/2011 | |
| CA | 2 739 310 A1 | 1/2011 | |
| EP | 2 458 378 A1 | 5/2012 | |
| EP | 2 698 633 A1 | 2/2014 | |
| EP | 2 717 054 A1 | 4/2014 | |
| JP | 0396801 * | 11/1990 | .......... G01N 33/538 |
| JP | 2010-286279 A | 12/2010 | |
| JP | 2017-134067 A | 8/2017 | |
| JP | 2019-4880 A | 1/2019 | |
| WO | WO 2012/133482 A1 | 10/2012 | |
| WO | WO 2012/161226 A1 | 11/2012 | |
| WO | WO 2018/062557 A1 | 4/2018 | |
| WO | WO 2018/088455 A1 | 5/2018 | |

OTHER PUBLICATIONS

Japanese Office Action for Japanese Application No. 2020-551153, dated Aug. 2, 2023, with an English translation.
Extended European Search Report for European Application No. 19871507.0, dated Jun. 8, 2022.
IBL, "Instruction for Use Code No. 27785, Mouse LRG Assay Kit—IBL", Immuno-Biological Laboratories Co., Ltd., Jul. 1, 2015, pp. 1-2, https://www.ibl-america.com/content/elisa/27785.pdf.
"Joint development of a serum biomarker (LRG) to rapidly assess disease activity in inflammatory bowel disease, how to measure LRG", National Institutes of Biomedical Innovation, Health and Nutrition, Apr. 20, 2016, total 2 pages, <URL: https://www.nibiohn.go.jp/information/nibio/2cf6eb2bcce3acbb7810dd7aaf78fdbc83436d80.pdf>.

(Continued)

*Primary Examiner* — Christina M Borgeest
(74) *Attorney, Agent, or Firm* — Birch, Stewart, Kolasch & Birch, LLP (57) ABSTRACT

An object of the present invention is to provide a measurement method and a reagent for measurement which can measure LRG in a biological sample simply in a short time. The present inventors have intensively studied to achieve the object and made findings that LRG in a biological sample can be measured simply in a short time by an immunoagglutination measurement method in which the biological sample is brought into contact with insoluble carrier particles carrying a first anti-LRG monoclonal antibody and insoluble carrier particles carrying a second anti-LRG monoclonal antibody in a liquid phase, and the invention has been thus completed.

11 Claims, 4 Drawing Sheets

(56) References Cited

OTHER PUBLICATIONS

International Search Report for PCT/JP2019/039564 mailed on Nov. 19, 2019.
O'Donnell et al., "Molecular characterization and expression analysis of leucine-rich α2-glycoprotein, a novel marker of granulocytic differentiation", Journal of Leukocyte Biology, Sep. 2002, vol. 72, pp. 478-485.
Written Opinion of the International Searching Authority for PCT/JP2019/039564 mailed on Nov. 19, 2019.
English translation of "Joint development of a serum biomarker (LRG) to rapidly assess disease activity in inflammatory bowel disease, how to measure LRG", National Institutes of Biomedical Innovation, Health and Nutrition, Apr. 20, 2016, 3 pages. <URL: https://www.nibiohn.go.jp/information/nibio/2cf6eb2bcce3acbb7810dd7aaf78fdbc83436d80.pdf>.
English translation of International Preliminary Report on Patentability and Written Opinion mailed Apr. 22, 2021, in PCT/JP2019/039564.
Written Opinion and Search Report issued Jan. 31, 2023, in Singapore Patent Application No. 11202103370R.
Chinese Office Action and Search Report for Chinese Application No. 201980065033.5, dated Feb. 27, 2024, with an English translation.
Korean Office Action for Korean Application No. 10-2021-7013480, dated May 21, 2024, with an English translation.

\* cited by examiner

IMMUNOASSAY AND MEASUREMENT REAGENT FOR LEUCINE-RICH ALPHA2 GLYCOPROTEIN

TECHNICAL FIELD

The present invention relates to an immunoassay and an immunoassay reagent for leucine-rich α2 glycoprotein. In particular, the invention relates to an immunoassay and an immunoassay reagent using insoluble carrier particles carrying substances having specific affinity to leucine-rich α2 glycoprotein.

BACKGROUND ART

It is reported that leucine-rich α2 glycoprotein (hereinafter, sometimes simply referred to as LRG) is one of serum proteins, is a glycoprotein of about 50 kDa and is secreted from neutrophils (Non-Patent Document 1).

Moreover, it is disclosed that LRG is useful as a biomarker for testing autoimmune diseases such as Behcet's disease (Patent Document 1).

Patent Document 1 shows that detection and quantitative determination of LRG have been conducted by proteome analysis and immunological methods and that the immunological methods include ELISA, Western blotting and the like using an anti-LRG monoclonal antibody.

As an assay reagent for the ELISA, for example, Human LRG Assay Kit-IBL (IBL Co, Ltd.) is commercially available. The ELISA reagent for measuring human LRG enables the quantitative determination of the LRG concentration of a sample by forming an immune complex through antigen-antibody reaction between an antibody which binds to LRG and LRG and measuring the amount of the label in the immune complex.

In general, the concentration of a target of measurement which is suitable for measurement by ELISA is in the range of pg/mL to ng/mL. Therefore, when the substance to be measured exists at a relatively high concentration of the order of μg/mL in a biological sample, pretreatment has been required for diluting the sample to a concentration at which the measurement reagent can exert the capability.

Moreover, it is necessary to dilute the sample by multiple separate stages to prevent an error due to high-rate dilution, and the complexity of the steps has been a problem. Specifically, with the commercial reagent above, it has been necessary to dilute the sample so that the LRG concentration of the sample falls in the constant range of 1.56 to 100 ng/mL. The dilution means that dilution at 1000 times is required, for example, when the maximum value of the concentration in human serum that can be possible in case of ulcerative colitis is 100 μg/mL.

Furthermore, it has been necessary to react the sample to be measured and the solid phase antibody for a long time with the conventional ELISA reagents for LRG measurement. For example, the commercial kit above requires one night for the primary reaction for bringing the solid phase antibody and the sample into contact with each other, and there has been no reagent which can measure LRG in a sample in a short time so far.

CITATION LIST

Patent Literature

Patent Document 1: JP-A-2010-286279

Non Patent Literature

Non-Patent Document 1: J Leukoc Biol. 2002, 72(3), 478-85, 2002

SUMMARY OF INVENTION

Technical Problem

An object of the invention is to provide a measurement method and a reagent for measurement which can measure LRG in a biological sample simply in a short time.

Solution to Problem

The present inventors have intensively studied to achieve the object and found that LRG in a biological sample can be measured simply in a short time without requiring pretreatment such as dilution when the reagent has a well-considered composition in an immunological measurement method in which the sample is brought into contact with insoluble carrier particles carrying a first anti-LRG monoclonal antibody and insoluble carrier particles carrying a second anti-LRG monoclonal antibody, specifically, in an immunoagglutination assay. The invention has been thus completed.

That is, the invention has the following constitutions.

<1> An immunological measurement method for leucine-rich α2 glycoprotein (LRG) in a biologically derived sample comprising:

bringing the sample into contact with at least insoluble carrier particles carrying a first anti-LRG monoclonal antibody and insoluble carrier particles carrying a second anti-LRG monoclonal antibody in a liquid phase.

<2> The measurement method according to <1>, wherein the insoluble carrier particles are latex particles having average particle sizes of 100 nm to 340 nm respectively.

<3> The measurement method according to <1> or <2>, wherein the insoluble carrier particles are latex particles having critical coagulation concentrations of 65 mM to 270 mM respectively.

<4> The measurement method according to any one of <1> to <3>, wherein the average particle sizes of the insoluble carrier particles carrying the first anti-LRG monoclonal antibody and the insoluble carrier particles carrying the second anti-LRG monoclonal antibody are the same.

<5> The measurement method according to any one of <1> to <4>, wherein the insoluble carrier particles carrying the first anti-LRG monoclonal antibody and the insoluble carrier particles carrying the second anti-LRG monoclonal antibody are contained in same amounts in the liquid phase.

<6> The measurement method according to any one of <1> to <5>, wherein the biologically derived sample is serum.

<7> The measurement method according to any one of <1> to <6>, wherein the immunoagglutination assay is a method based on a homogeneous method.

<8> The measurement method according to any one of <1> to <7>, wherein the step of bringing the biologically derived sample into contact with the insoluble carrier particles carrying the first anti-LRG monoclonal antibody and the insoluble carrier particles carrying the second anti-LRG monoclonal antibody in the liquid phase comprises following steps:

(1) bringing the sample and a first reagent containing a buffer into contact with each other in the liquid phase; and (2) adding a second reagent containing the insoluble carrier particles carrying the first anti-LRG monoclonal antibody and the insoluble carrier particles carrying the second anti-LRG monoclonal antibody to the liquid phase after step (1).

<9> The measurement method according to <8>, wherein the salt concentration of the liquid phase of (1) is 700 to 900 mM.

<10> The measurement method according to any one of <1> to <9> further comprising:
optically measuring a degree of agglutination of a complex of LRG and the insoluble carrier particles carrying the anti-LRG monoclonal antibodies.

<11> The measurement method according to <10>, wherein the step of optical measuring is a step of measuring an intensity of scattered light, an absorbance or an intensity of transmitted light with an optical device.

<12> A reagent for measuring LRG in a blood sample by an immunological measurement method comprising:
at least insoluble carrier particles carrying a first anti-LRG monoclonal antibody and insoluble carrier particles carrying a second anti-LRG monoclonal antibody.

<13> The measurement reagent according to <12>, wherein the insoluble carrier particles are latex particles having average particle sizes of 100 nm to 340 nm respectively.

<14> The measurement reagent according to <12> or <13>, wherein the insoluble carrier particles are latex particles having critical coagulation concentrations of 65 mM to 270 mM respectively.

<15> The measurement reagent according to any one of <12> to <14>, wherein the average particle sizes of the insoluble carrier particles carrying the first anti-LRG monoclonal antibody and the insoluble carrier particles carrying the second anti-LRG monoclonal antibody are the same.

<16> The measurement reagent according to any one of <12> to <15>, wherein the insoluble carrier particles carrying the first anti-LRG monoclonal antibody and the insoluble carrier particles carrying the second anti-LRG monoclonal antibody are contained in same amounts.

<17> The measurement reagent according to any one of <12> to <16>, wherein the biologically derived sample is serum.

<18> The measurement reagent according to any one of <12> to <17>, wherein the immunoagglutination assay is a method based on a homogeneous method.

<19> A reagent kit for measuring LRG in a blood sample by an immunoagglutination assay comprising:
(1) a first reagent containing a buffer and
(2) a second reagent containing insoluble carrier particles carrying a first anti-LRG monoclonal antibody and insoluble carrier particles carrying a second anti-LRG monoclonal antibody.

<20> The reagent kit according to <19>, wherein the insoluble carrier particles are latex particles having average particle sizes of 100 nm to 340 nm respectively.

<21> The reagent kit according to <19> or <20>, wherein the insoluble carrier particles are latex particles having critical coagulation concentrations of 65 mM to 270 mM respectively.

<22> The reagent kit according to any one of <19> to <21>, wherein the average particle sizes of the insoluble carrier particles carrying the first anti-LRG monoclonal antibody and the insoluble carrier particles carrying the second anti-LRG monoclonal antibody are the same.

<23> The reagent kit according to any one of <19> to <22>, wherein the second reagent of (2) contains the insoluble carrier particles carrying the first anti-LRG monoclonal antibody and the insoluble carrier particles carrying the second anti-LRG monoclonal antibody in same amounts.

<24> The reagent kit according to any one of <19> to <23>, wherein the first reagent of (1) contains a salt in such an amount that a salt concentration of a reaction liquid phase becomes 700 to 900 mM.

<25> The reagent kit according to any one of <19> to <24> further comprising:
(3) LRG as a standard antigen and/or a control.

Advantageous Effects of Invention

According to the invention, a measurement method and a reagent for measurement of LRG in a biological sample which can provide results more simply in a short time is provided.

DESCRIPTION OF EMBODIMENTS (Immunoagglutination Assay)
An immunoagglutination assay is a kind of immunoassay which uses insoluble carrier particles on which a substance having specific affinity for the subject to be measured such as an antigen or an antibody is immobilized and measures the antigen or the antibody, and the assay is widely used in the field of clinical examination. Latex or the like is mainly used for the insoluble carrier particles, and in such a case, the assay is specifically called a latex immunoagglutination assay (LTIA).

Methods for measuring LRG by LTIA can be roughly classified into methods in which latex particles on which monoclonal antibodies to LRG are immobilized and LRG as the antigen are reacted to form a sandwich-shaped immune complex and in which LRG is measured by the degree of agglutination of the latex particles resulting from the immune complex formation, and methods in which antigen-immobilized latex particles and LRG in a sample are competed to inhibit the formation of an immune complex of the latex particles and the antibody and in which LRG is measured by the degree of inhibition of agglutination of the latex particles resulting from the inhibition of the immune complex formation.

(Sample)

The sample of the invention is not particularly limited as long as the sample is a biological sample but is typically a blood sample, and examples include whole blood, serum and plasma. Plasma includes heparin-plasma, EDTA-plasma and the like.

(Substance to be Measured)

The substance to be measured in the invention is leucine-rich α2 glycoprotein (LRG).

(Measurement Method)

In a measurement method using immunoagglutination represented by LTIA, the substance to be tested can be measured by optically or electrochemically observing the degree of generated agglutination. An optical observation method includes a method for measuring the intensity of scattered light, the absorbance or the intensity of transmitted light with an optical device (endpoint method, rate method or the like). The concentration of LRG (quantitative value) contained in the sample is calculated by comparing the measured value of the absorbance or the like obtained by measuring the sample with the measured value of the absorbance or the like obtained by measuring a standard substance (a sample with a known LRG concentration). In this regard, the absorbance or the like of transmitted light, scattered light or the like may be measured by single wavelength measurement or dual-wavelength measurement (the difference or the ratio resulting from two wavelengths). The wavelength for the measurement is generally determined in the range of 500 nm to 800 nm.

LRG in the sample of the invention may be measured by a hand process or using an apparatus such as a measurement apparatus. The measurement apparatus may be a general-purpose automated analyzer or a single-purpose measurement apparatus (a special purpose apparatus). The measurement is preferably conducted by a method using multiple operational steps such as a two-step method (dual-reagent method).

(Anti-LRG Monoclonal Antibodies)

The monoclonal antibodies of the invention can be obtained by methods known to one skilled in the art. That is, the monoclonal antibodies can be easily produced by dissolving human LRG as the antigen in a solvent such as phosphate-buffered physiological saline and administering the solution to an animal for immunization. When necessary, an appropriate adjuvant may be added to the solution, and then an animal may be immunized using the emulsion. As the adjuvant, generally used adjuvants such as water-in-oil emulsion, water-in-oil-in-water emulsion, oil-in-water emulsion, liposome and aluminum hydroxide gel as well as proteins and peptide substances derived from biological components and the like may be used. For example, incomplete Freund's adjuvant, complete Freund's adjuvant or the like can be suitably used. The administration route, the dosage and the timing of administration of the adjuvant are not particularly limited but desirably selected appropriately so that desired immune response can be enhanced in the animal to be immunized with the antigen.

The kind of animal used for immunization is not particularly limited, either, but is preferably a mammal. For example, mice, rats, cows, rabbits, goats, sheep and the like can be used, and mice can be used more preferably. An animal may be immunized according to a general method and can be immunized for example by injecting a solution of the antigen, preferably a mixture with an adjuvant, subcutaneously, intracutaneously, intravenously or intraperitoneally to the animal. Because the immune response generally differs with the kind and the line of the animal to be immunized, the immunization schedule is desirably set appropriately depending on the animal to be used. The administration of the antigen is preferably repeated several times after the first immunization.

When the monoclonal antibodies are obtained, the following procedures follow, but the method for producing the monoclonal antibodies themselves is not limited to the procedures and can be in accordance with the method described for example in Antibodies, A Laboratory Manual (Cold Spring Harbor Laboratory Press, (1988)).

After the final immunization, spleen cells or lymph node cells, which are antibody-producing cells, are taken out of the immunized animal, and hybridomas can be produced by cell fusion with myeloma cells having high growth potential. Cells with high antibody-producing potential (quality/amount) are preferably used for the cell fusion, and the myeloma cells preferably have compatibility with the animal from which the antibody-producing cells to be fused are derived. The cells can be fused according to a method known in the field, but for example, a polyethylene glycol method, a method using Sendai virus, a method using current and the like can be employed. The obtained hybridomas can be proliferated according to a known method, and a desired hybridoma can be selected while the properties of the produced antibody are examined. The hybridoma can be cloned by a known method such as limiting dilution analysis or soft agar analysis, for example.

The selection of hybridomas producing the first and second monoclonal antibodies is explained. The hybridomas can also be selected efficiently at the selection stage considering the conditions under which the produced antibodies are used for the actual measurement. For example, the hybridomas are obtained by selecting hybridomas producing an antibody that reacts with human LRG by ELISA, RIA, Biacore assay or the like. Specifically, monoclonal antibodies in a culture supernatant are first reacted with immobilized human LRG, and hybridomas producing monoclonal antibodies that have high reactivity with human LRG are then selected by antigen-immobilized ELISA in which a labelled anti-IgG antibody is reacted.

By culturing a hybridoma which is selected as described above in a large scale, a monoclonal antibody having desired characteristics can be produced. The large-scale cultivation method is not particularly limited, but examples include a method for culturing the hybridoma in an appropriate medium and thus producing the monoclonal antibody in the medium, a method for intraperitoneally injecting the hybridoma to a mammal, proliferating the hybridoma and producing the antibody in the ascites and the like. The monoclonal antibodies can be purified by an appropriate combination of anion-exchange chromatography, affinity chromatography, ammonium sulfate fractionation, PEG fractionation, ethanol fractionation and the like, for example.

As the antibodies of the invention, functional fragments of antibodies having antigen-antibody reactivity can also be used in addition to the whole antibody molecules, and those obtained through the immunization step of an animal described above, those obtained using genetic recombination technique and chimeric antibodies can also be used. Examples of functional fragments of an antibody include F(ab')₂, Fab' and the like, and such functional fragments can be produced by processing an antibody obtained as described above with a protease (for example, pepsin, papain or the like).

(Insoluble Carrier Particles)

The insoluble carrier particles used in the invention may be insoluble carrier particles which can carry an anti-LRG monoclonal antibody and which can measure LRG in a sample. Examples include latex particles, magnetic particles, metal particles and the like, but latex particles are preferable of those examples.

The average particle sizes and the critical coagulation concentrations of the insoluble carrier particles are appropriately determined considering the concentration of LRG in the sample, the detection sensitivity of the measurement device or the like.

The average particle sizes of the insoluble carrier particles are preferably 100 nm to 340 nm, more preferably 150 nm to 260 nm.

Regarding the critical coagulation concentrations of the insoluble carrier particles, those having a critical coagulation concentration of preferably 65 mM to 270 mM, more preferably 150 mM to 270 mM, are appropriately selected.

(Latex Particles)

The latex particles, which are a preferable example of the insoluble carrier particles used in the invention, are not particularly limited as long as the latex particles are generally used as an immunological measurement reagent. The latex particles can be obtained by polymerization or co-polymerization of various monomers. Examples of the monomers here include polymerizable unsaturated aromatic compounds such as polymerizable monomers having a phenyl group including styrene, α-methylstyrene, o-methylstyrene, p-methylstyrene, p-chlorostyrene, 4-vinylbenzoate, divinylbenzene, vinyltoluene and the like, polymerizable monomers having a phenyl group and a sulfonate including styrene sulfonate, divinyl benzene sulfonate, o-methyl styrene sulfonate, p-methyl styrene sulfonate and the like and polymerizable monomers having a naphthyl group including 1-vinylnaphthalene, 2-vinylnaphthalene, α-naphthyl (meth) acrylate, β-naphthyl (meth)acrylate and the like, polymerizable unsaturated carboxylic acids such as (meth)acrylic acid, itaconic acid, maleic acid and fumaric acid, polymerizable unsaturated carboxylate esters such as methyl (meth) acrylate, ethyl (meth)acrylate, n-butyl (meth) acrylate, 2-hydroxyethyl (meth) acrylate, glycidyl (meth)acrylate, ethylene glycol-di-(meth)acrylate ester and tribromophenyl (meth)acrylate, unsaturated carboxylic amides, polymerizable unsaturated nitriles, vinyl halides and conjugated dienes such as (meth) acrylonitrile, (meth)acrolein, (meth) acrylamide, N-methylol-(meth) acrylamide, methylenebis(meth) acrylamide, butadiene, isoprene, vinyl acetate, vinylpyridine, N-vinylpyrrolidone, vinyl chloride, vinylidene chloride and vinyl bromide and the like. The monomers are appropriately selected by the required surface characteristics, the specific gravities and the like. A kind thereof can be used alone, or a mixture of two or more kinds thereof can be used.

The average particle sizes of the latex particles can be analyzed using laser diffraction/scattering method (LS method), the Coulter principle, dynamic light scattering-photon correlation spectroscopy, an electron microscope or the like.

Regarding the average particle sizes of the latex particles, those having average particle sizes of preferably 100 nm to 340 nm, more preferably 150 nm to 260 nm, are appropriately selected. The reasons are as follows: when the average particle sizes are smaller than 100 nm, the sensitivity in the low concentration to middle concentration range decreases, and accurate measurement is difficult; and when the average particle sizes exceed 340 nm, the so-called hook effect is caused at a high concentration, which causes a phenomenon whereby a value lower than the actual concentration is obtained, although the sensitivity at a low concentration increases.

The critical coagulation concentration of latex particles means the maximum concentration of a salt at which latex does not agglutinate and means the salt concentration which is one step lower than the salt concentration at which latex particles self-agglutinate completely when a salt is stepwisely added to the latex particles that are not sensitized with an antibody. For example, aqueous sodium phosphate solutions (pH7.4) having concentrations that are different by 10 mM in the range of 10 to 400 mM are prepared, and latex particles in an amount which results in the final concentration of 1% (W/V) are added to the aqueous sodium phosphate solutions with the different concentrations and stirred. The solutions are observed visually after one minute to determine whether or not the latex has self-agglutinated, and the concentration of the aqueous sodium phosphate solution that is one step lower than the concentration at which the latex has self-agglutinated completely is determined as the critical coagulation concentration (maximum non-coagulation concentration).

Regarding the critical coagulation concentrations (the concentrations of the aqueous sodium phosphate solutions) of the latex particles, those having critical coagulation concentrations of preferably 65 mM to 270 mM, more preferably 150 mM to 270 mM, are appropriately selected. It is difficult to maintain the dispersion of the latex particles when the critical coagulation concentrations are smaller than 65 mM, while immune response is not caused easily, and the latex particles do not agglutinate when the critical coagulation concentrations are 270 mM or more.

The critical coagulation concentration of latex particles can be controlled by appropriately changing the weight ratio of the raw materials. For example, styrene latex is obtained through co-polymerization of a certain amount of a polymerizable monomer having a phenyl group such as styrene and a certain amount of a polymerizable monomer having a phenyl group and a sulfonate such as sodium styrene sulfonate in an aqueous medium, and the critical coagulation concentration can be controlled by changing the mixing ratio of styrene and sodium styrene sulfate in this case.

The materials and the particle sizes of the latex particles used can be appropriately selected to obtain desired properties such as increased sensitivity, and those having different materials and different particle sizes can also be used in combination.

Moreover, the concentrations of the latex particles during the agglutination reaction measurement in the invention are not particularly limited and can be appropriately set depending on the desired sensitivity and properties.

(Anti-LRG Monoclonal Antibody-Carrying Insoluble Carrier Particles)

An antibody to LRG can be immobilized and carried on insoluble carrier particles such as latex particles by a known method such as a physical adsorption (hydrophobic bonding) method, a chemical bonding method or a combination thereof. The following explanation is given using latex as a typical example of the insoluble carrier particles.

The physical adsorption method can be conducted according to a known method by mixing an antibody to LRG and latex particles in a solution such as a buffer and bringing the antibody and the latex particles into contact with each other or by bringing an antibody to LRG dissolved in a buffer or the like into contact with a carrier.

The chemical bonding method can be conducted according to a known method described in "Extra Special Issue of Clinical Pathology, No. 53, Immunoassay for Clinical Examination—Techniques and Applications—" edited by The Japanese Society of Clinical Pathology, Clinical Pathology Publication Society, issued in 1983; "New Courses in Biochemical Experiment 1, Protein IV" edited by The Japanese Biochemical Society, Tokyo Kagaku Dojin, issued in 1991 or the like, by mixing and bringing a substance specifically binding to LRG and a carrier into contact with a divalent crosslinking reagent such as glutaraldehyde, carbodiimide, an imide ester or maleimide and reacting the amino groups, the carboxyl groups, the thiol groups, the aldehyde groups, the hydroxyl groups or the like of the substance specifically binding to LRG and the carrier with the divalent crosslinking reagent.

At least two kinds of antibody to a specific substance carried on the latex particles are required to form a sandwich shape. That is, two or more monoclonal antibodies having different recognition sites are used as the anti-LRG monoclonal antibodies.

It is necessary that the first monoclonal antibody and the second monoclonal antibody are carried on different insoluble carrier particles.

In the invention, the concentrations of the insoluble carrier particles carrying the first anti-LRG monoclonal antibody and the insoluble carrier particles carrying the second anti-LRG monoclonal antibody can be appropriately set depending on the desired sensitivity and properties as described above, but the insoluble carrier particles are preferably contained in same amounts in the reaction liquid phase.

Moreover, in the invention, the average particle sizes of the insoluble carrier particles carrying the first anti-LRG monoclonal antibody and the insoluble carrier particles carrying the second anti-LRG monoclonal antibody are each preferably 100 nm to 340 nm as described above. The average particle sizes are preferably similar, more preferably the same. That the average particle sizes are similar means that one of the average particle sizes falls in the range of 80 to 120% of the other average particle size, and that the average particle sizes are the same means that one of the average particle sizes falls in the range of 90 to 110% of the other average particle size.

When treatment is necessary to inhibit spontaneous agglutination of the latex particles, non-specific reaction or the like, the carrier may be subjected to blocking (masking) by a known method such as contacting or covering the surface of the latex particles with a protein such as bovine serum albumin (BSA), casein, gelatin, egg albumin or salts thereof, a surfactant, defatted milk powder or the like.

(Contact)

That the sample containing LRG and the latex particles carrying the anti-LRG monoclonal antibodies are brought into contact with each other in a liquid phase typically means (1) to (4) below.

(1) An embodiment in which, after mixing the sample and a buffer, the latex particles carrying the first anti-LRG monoclonal antibody and the second anti-LRG monoclonal antibody are mixed into the mixture solution.

(2) An embodiment in which the sample, a buffer, the latex particles carrying the first anti-LRG monoclonal antibody and the latex particles carrying the second anti-LRG monoclonal antibody are mixed at the same time.

(3) An embodiment in which the latex particles carrying the first anti-LRG monoclonal antibody are mixed after mixing the sample and a buffer and in which the latex particles carrying the second anti-LRG monoclonal antibody are then mixed.

(4) An embodiment in which the sample is added and mixed in the end in (1) to (3).

(Reagent for Measurement)

The reagent for measurement of the invention is a reagent for measuring LRG in a blood sample by an immunoagglutination assay and contains at least insoluble carrier particles carrying a first anti-LRG monoclonal antibody and insoluble carrier particles carrying a second anti-LRG monoclonal antibody. Typically, the reagent comprises two or more constituent reagents. At least one of the constituent reagents contains the latex particles carrying the anti-LRG monoclonal antibodies, and another constituent reagent contains a buffer. Moreover, the reagent for measurement of the invention is a liquid reagent.

In particular, the reagent for measurement of the invention is preferably a two-reagent type including a first reagent and a second reagent. For example, the first reagent of the two-reagent type contains a buffer for diluting the biologically derived sample containing LRG, and the second reagent is a reagent solution containing the latex particles carrying the first anti-LRG monoclonal antibody and the latex particles carrying the second anti-LRG monoclonal antibody.

When the reagent for measurement of the invention is a three-reagents type including a first reagent, a second reagent and a third reagent, for example, the first reagent contains a buffer or the like. The second reagent is a reagent solution containing the latex particles carrying the first anti-LRG monoclonal antibody, and the third reagent is a reagent solution containing the latex particles carrying the second anti-LRG monoclonal antibody.

The buffer contained in the measurement reagent of the invention may be a buffer that is generally used, and examples include tris-hydrochloric acid, boric acid, phosphoric acid, acetic acid, citric acid, succinic acid, phthalic acid, glutaric acid, maleic acid, glycine, a salt thereof and the like as well as Good's buffers such as MES, Bis-Tris, ADA, PIPES, ACES, MOPSO, BES, MOPS, TES and HEPES and the like.

The concentration of the buffer component may be in a concentration range in which spontaneous agglutination of the insoluble carrier particles in the reagent is not caused and in which the desired immune response is caused, and the concentration in the reaction solution may be 100 mM or more and is preferably 200 mM or more, more preferably 300 mM or more, further more preferably 400 mM or more.

The measurement reagent of the invention desirably further contains a salt. The kind of the salt is desirably an inorganic salt, and examples of the inorganic salt include sodium chloride, calcium chloride and the like.

The salt concentration may be in a concentration range in which spontaneous agglutination of the insoluble carrier particles in the reagent is not caused and in which the desired immune response is caused, and the lower limit of the concentration may be 100 mM or more in the reaction solution and is preferably 300 mM or more, more preferably 500 mM or more, furthermore preferably 700 mM or more. The upper limit of the concentration is preferably 2000 mM or less in the reaction solution, more preferably 1500 mM or less, further more preferably 1000 mM or less, most preferably 900 mM or less.

The range of the concentration in the reaction solution is preferably 100 to 1500 mM, more preferably 300 to 1000 mM, further more preferably 500 to 1000 mM, most preferably 700 to 900 mM.

The measurable range (measurement range) of the measurement reagent of the invention may be around 10 to 80 µg/mL, desirably 5.0 to 100 µg/mL to measure LRG as a diagnostic marker.

(Reagent Kit)

The reagent kit of the invention is characterized by including at least elements (1) and (2) below.

(1) A first reagent containing a buffer.

(2) A second reagent containing at least insoluble carrier particles carrying a first anti-LRG monoclonal antibody and insoluble carrier particles carrying a second anti-LRG monoclonal antibody.

In the reagent kit of the invention, (3) LRG as a standard antigen or a control can be included in addition to the measurement reagents above.

A sample pretreatment reagent for pretreating the sample may also be included. The sample pretreatment reagent can be contained in the first reagent of (1) containing a buffer or can also be included as an element other than (1) and (2).

The reagent kit can further include a user guide, a sample collection tool (a collection pipette, a syringe, a cotton swab, a filter and the like), a sample diluent and a sample extraction solution.

(Homogeneous Method)

In the invention, the homogeneous method refers to a measurement method for specifically detecting the reaction that advances in the mixed solution of the sample and the reagent solution (reaction solution) without conducting B/F (bound/free) separation and means a measurement method named in comparison to a heterogeneous measurement method, in which the main reaction is advanced and detected after completely washing/removing the excess components which have not involved in the measurement reaction by a B/F separation operation. Therefore, that "the immunoagglutination assay is a method based on a homogeneous method" as in the invention means that step (3) is "a step of measuring the agglutination reaction of LRG and the insoluble carrier particles without a washing/separation step during step (2) or after step (2)" in typical steps (1) to (3) below.

(1) A step of bringing the sample and a buffer into contact with each other in a liquid phase.

(2) A step of adding insoluble carrier particles carrying anti-LRG monoclonal antibodies to the liquid phase after step (1).

(3) A step of measuring the agglutination reaction of LRG and the insoluble carrier particles after step (2).

(Other Reagent Components)

The reagent of the invention may contain a polymer such as polyethylene glycol, polyvinylpyrrolidone and a phospholipid polymer as a component that supplements the formation of agglutination of the insoluble carrier particles. Moreover, as a component that controls the formation of agglutination, a kind or a combination of generally used components such as proteins, amino acids, saccharides, metal salts, surfactants, reducing substances and chaotropic substances may also be contained.

EXAMPLES

The invention is explained in detail below referring to Examples, but the invention should not be construed as being limited to the Examples.

Test Example 1

The particle sizes of the insoluble carrier particles used for measuring LRG concentrations were changed, and whether or not a concentration-dependent change in absorbance would be observed and whether or not a calibration curve could be drawn were examined.

1. Reagents (1) First Reagent

The reagent contains the components shown below. The pH was controlled to 6.5 to 7.5.
HEPES
1M NaCl
1.0% BSA
0.05% Proclin950

(2) Second Reagent (2-1) Prescription Example 1

The two kinds of anti-LRG monoclonal antibody-sensitized latex particle solution below were mixed in same amounts and diluted with 10 mM HEPES buffer (pH7.2) in a manner that the absorbance at a wavelength of 570 nm became 4.5 Abs., and a second reagent was thus obtained.

(i) First Anti-LRG Monoclonal Antibody (Kan10)-Sensitized Latex Particle Solution To a 1% polystyrene latex solution (20 mM glycine buffer) having an average particle size of 343 nm and a critical coagulation concentration of 60 mM, the same amount of an anti-LRG monoclonal antibody (Kan10) solution which had been diluted with 50 mM glycine buffer to 0.71 mg/mL was added, and the mixture was stirred at 4° C. for two hours. Then, the same amount of a synthetic polymer (Blockmaster CE210 manufactured by JSR) was added, and the mixture was stirred at 4° C. for an hour. Subsequently, 1/10 amount of 10% BSA solution dissolved in purified water was added, and the mixture was stirred at 4° C. for an hour. An anti-LRG monoclonal antibody (Kan10)-sensitized latex solution was thus produced.

(ii) Second Anti-LRG Monoclonal Antibody-Sensitized Latex Particle Solution

An anti-LRG monoclonal antibody (Kan11)-sensitized latex particle solution was produced by the same method as that of (i) above using polystyrene latex having an average particle size of 343 nm and a critical coagulation concentration of 60 mM.

(iii) Physical Properties of Latex Particles (a) Measurement Method of Particle Sizes of Latex Particles The latex particle sizes were analyzed with Laser diffraction/scattering particle size distribution analyzer LS13320 (manufactured by Beckman Coulter).

(b) Measurement Method of Critical Coagulation Concentrations of Latex Particles Aqueous sodium phosphate solutions (pH7.4) having concentrations that were different by 10 mM in the range of 10 to 400 mM were prepared, and latex particles in an amount which resulted in the final concentration of 1% (W/V) were added to the aqueous sodium phosphate solutions with the different concentrations and stirred. Then, the solutions were observed visually after one minute to determine whether or not the latex self-agglutinated, and the concentration of the aqueous sodium phosphate solution that was one step lower than the concentration at which the latex self-agglutinated completely was determined as the critical coagulation concentration.

(2-2) Prescription Examples 2 to 6

The same procedures were conducted except that the latex particles of Prescription Example 1 were changed as follows.

Prescription Example 2: The average particle sizes were 305 nm, and the critical coagulation concentrations were 70 mM.

Prescription Example 3: The average particle sizes were 251 nm, and the critical coagulation concentrations were 260 mM.

Prescription Example 4: The average particle sizes were 207 nm, and the critical coagulation concentrations were 180 mM.

Prescription Example 5: The average particle sizes were 194 nm, and the critical coagulation concentrations were 230 mM.

Prescription Example 6: The average particle sizes were 121 nm, and the critical coagulation concentrations were 210 mM.

2. Samples to be Tested

Purified LRG (manufactured by Bio Vendor Laboratory medicine) in amounts resulting in 0, 5.0, 10.0, 23.0, 50.0 and 100.0 μg/mL was added to physiological saline.

3. Measurement Method

The first reagents and the second reagents of the Prescription Examples were each combined, and the samples containing LRG at known concentrations were measured using Hitachi 7180 automated analyzer. Specifically, 150 μL of the first reagent was added to 2.5 μL of a sample, and the mixture was incubated at 37° C. for five minutes. Then, 50 μL of the second reagent was added, and the mixture was stirred. The change in absorbance resulting from the formation of agglutination was measured for five minutes after that at a dominant wavelength of 570 nm and a complementary wavelength of 800 nm, and the change in absorbance was measured. A calibration curve was drawn from the measured absorbances, and $R^2$ (coefficient of determination) was determined.

4. Measurement Conditions

The parameter conditions of Hitachi 7180 automated analyzer are shown below.
(1) Liquid Amount: specimen-first reagent-second reagent; 2.5 μL-150 μL-50 μL
(2) Analysis Method: 2-point end method (photometric points 19-34)
(3) Measurement Wavelengths: dominant wavelength of 570 nm/complementary wavelength of 800 nm
(4) Calibration: spline

5. Measurement Results and Discussion

The results are shown in FIG. 1 to FIG. 6.
According to the results, in Prescription Example 1, although the hook effect was observed at a high LRG concentration (100 μg/ml), the absorbance increased in a concentration-dependent manner at low to middle concentrations. In Prescription Examples 2 to 6, the absorbances increased in a concentration-dependent manner at a low concentration to a high concentration, and the $R^2$ values were 0.99 or more. In particular, the $R^2$ values of Prescription Examples 3, 4 and 5 were 0.996 or more, which are particularly excellent.

From the above results, it was found that accurate measurement is possible in the concentration range which covers the entire LRG concentration distribution in human serum when the average particle sizes of the latex particles are 100 nm to 340 nm and that, in particular, measurement with higher accuracy is possible when the average particle sizes are 150 nm to 260 nm.

It was also found that accurate measurement is possible in the concentration range which covers the entire LRG concentration distribution in human serum when the critical coagulation concentrations are 65 mM to 270 mM and that, in particular, measurement with higher accuracy is possible when the critical coagulation concentrations are 150 mM to 270 mM.

Test Example 2

In order to examine whether or not specimens similar to an actual specimen could be measured, simulated LRG specimens with known concentrations were prepared by adding purified LRG to pooled serum, and the concentrations of LRG were measured.

1. Reagents

The reagents of Prescription Examples 2 to 6 of Test Example 1 were used.

2. Samples to be Tested (1) Pooled serum was used as panel specimen L.
(2) Purified LRG in an amount resulting in 28.2 μg/mL was added to pooled serum and used as panel specimen M.
(3) Purified LRG in an amount resulting in 63.1 μg/mL was added to pooled serum and used as panel specimen H.

3. Measurement Method and Measurement Conditions

The test method and the measurement conditions are the same as those in Test Example 1. Using the calibration curves drawn in Test Example 1, the concentrations of the panel specimens were determined, and the relative ratios (%) to the known concentrations were calculated.

4. Measurement Results and Discussion

The results are shown in Table 1.
According to the results, it was found that simulated specimens which are similar to an actual specimen can be measured accurately using the reagents of Prescription Examples 2 to 6. In particular, Prescription Examples 3 to 5 had extremely high accuracy of relative ratios to the known concentrations of 99%.

From the above results it was found that accurate measurement is possible when the average particle sizes of the latex particles are 100 nm to 340 nm and that, in particular, measurement with higher accuracy is possible when the average particle sizes are 150 nm to 260 nm.

It was also found that accurate measurement is possible when the critical coagulation concentrations of latex are 65 mM to 270 mM and that, in particular, measurement with higher accuracy is possible when the critical coagulation concentrations are 150 mM to 270 mM.

TABLE 1

| Panel Specimen | LRG Concentration | Prescription Example 2 | Prescription Example 3 | Prescription Example 4 | Prescription Example 5 | Prescription Example 6 |
| --- | --- | --- | --- | --- | --- | --- |
| Panel L | 10.3 | 11.1 (108%) | 10.1 (98%) | 10.4 (101%) | 10.4 (101%) | 9.9 (96%) |
| Panel M | 28.2 | 29.7 (105%) | 27.3 (97%) | 28.8 (102%) | 28.4 (101%) | 27.2 (96%) |
| Panel H | 63.1 | 57.2 (91%) | 62.5 (99%) | 62.2 (99%) | 62.3 (99%) | 67.7 (107%) |

* The unit of the LRG concentrations is µg/mL, and the values in the brackets are the relative ratios (%) to the known concentrations.

Test Example 3

It was confirmed that LRG can be measured as a marker by the measurement method of the invention using specimens of healthy individuals and specimens of patients.

1. Reagents

The reagents of Prescription Example 5 of Test Example 1 were used.

2. Samples to be Tested (1) Serum Specimens of Healthy Individuals
   Seven specimens purchased from PROMEDDEX.
(2) Serum Specimens of Ulcerative Colitis Patients (Mild (Remission Phase))
   Thirteen specimens purchased from Bioreclamtion.
(3) Serum Specimens of Ulcerative Colitis Patients (Severe (Active Stage))
   Five specimens purchased from Bioreclamtion and Proteogenex.

3. Measurement Method and Measurement Conditions

The measurement method and the measurement conditions are the same as those in Test Example 1.

4. Measurement Results and Discussion

Figure 1:
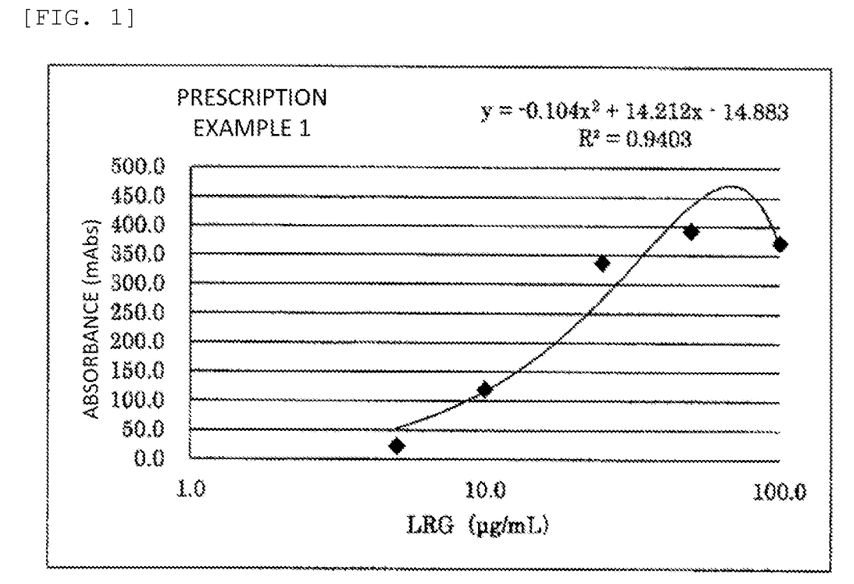
FIG. 1 A graph showing the results of measurement of samples containing LRG at known concentrations using the combination of a first reagent and a second reagent of Prescription Example 1 using an automated analyzer.
Figure 2:
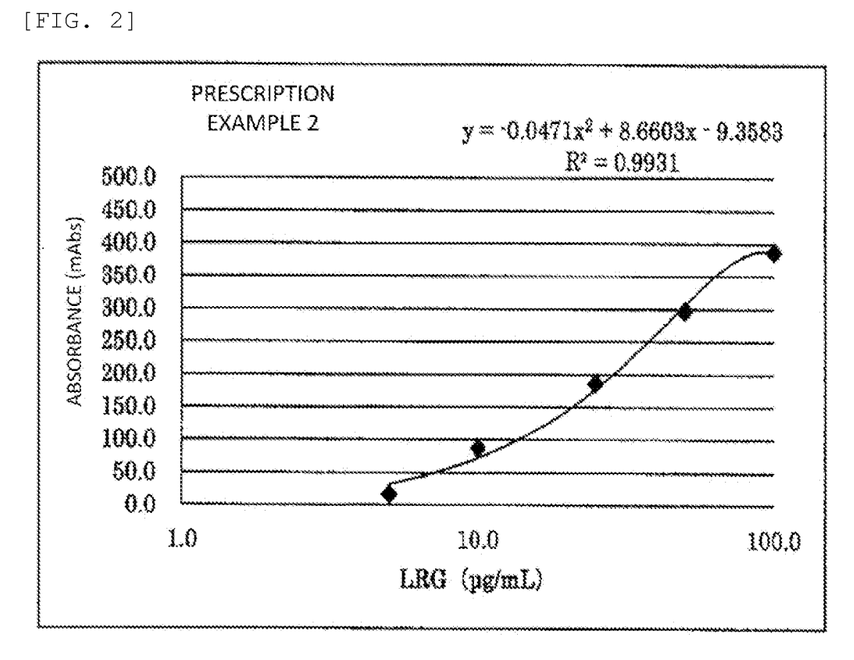
FIG. 2 A graph showing the results of measurement of samples containing LRG at known concentrations using the combination of a first reagent and a second reagent of Prescription Example 2 using an automated analyzer.
Figure 3:
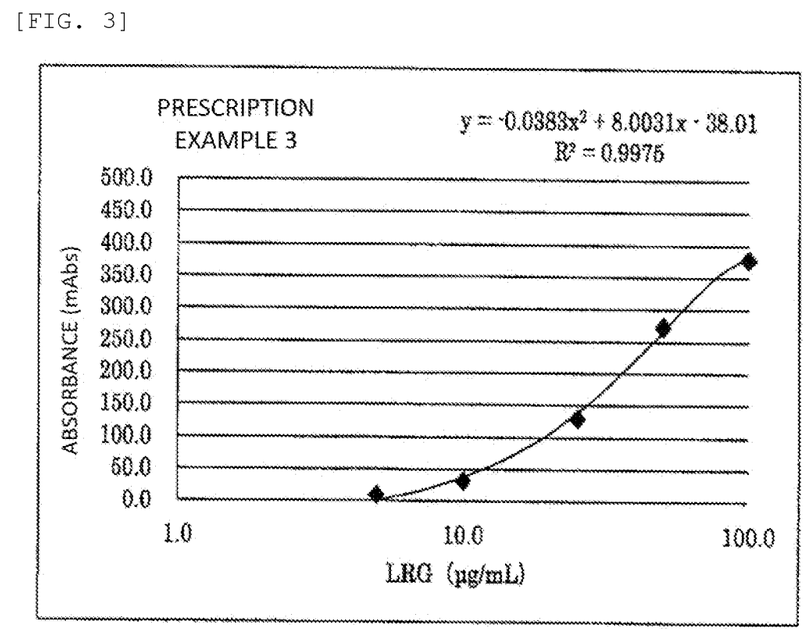
FIG. 3 A graph showing the results of measurement of samples containing LRG at known concentrations using the combination of a first reagent and a second reagent of Prescription Example 3 using an automated analyzer.
Figure 4:
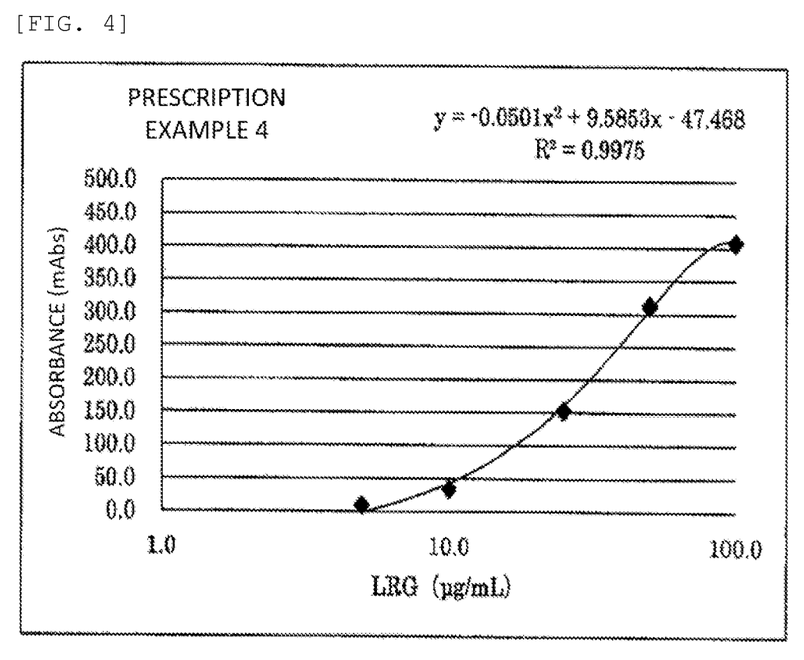
FIG. 4 A graph showing the results of measurement of samples containing LRG at known concentrations using the combination of a first reagent and a second reagent of Prescription Example 4 using an automated analyzer.
Figure 5:
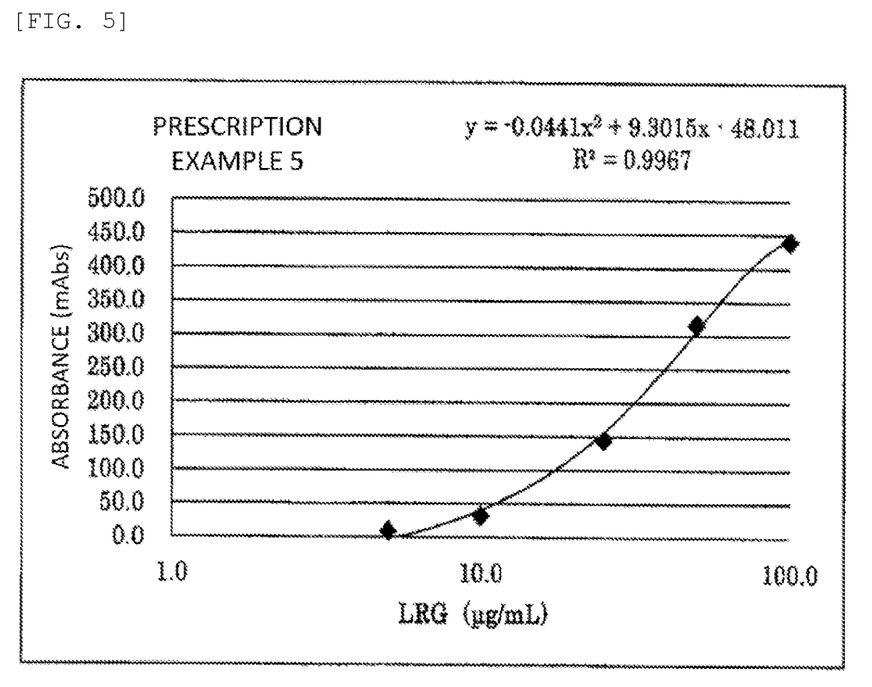
FIG. 5 A graph showing the results of measurement of samples containing LRG at known concentrations using the combination of a first reagent and a second reagent of Prescription Example 5 using an automated analyzer.
Figure 6:
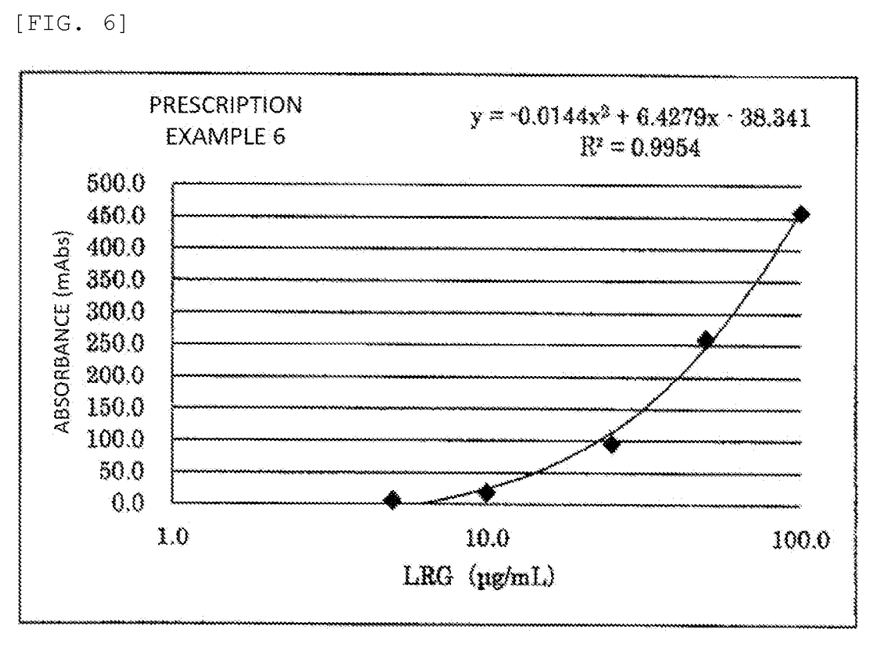
FIG. 6 A graph showing the results of measurement of samples containing LRG at known concentrations using the combination of a first reagent and a second reagent of Prescription Example 6 using an automated analyzer.
Figure 7:
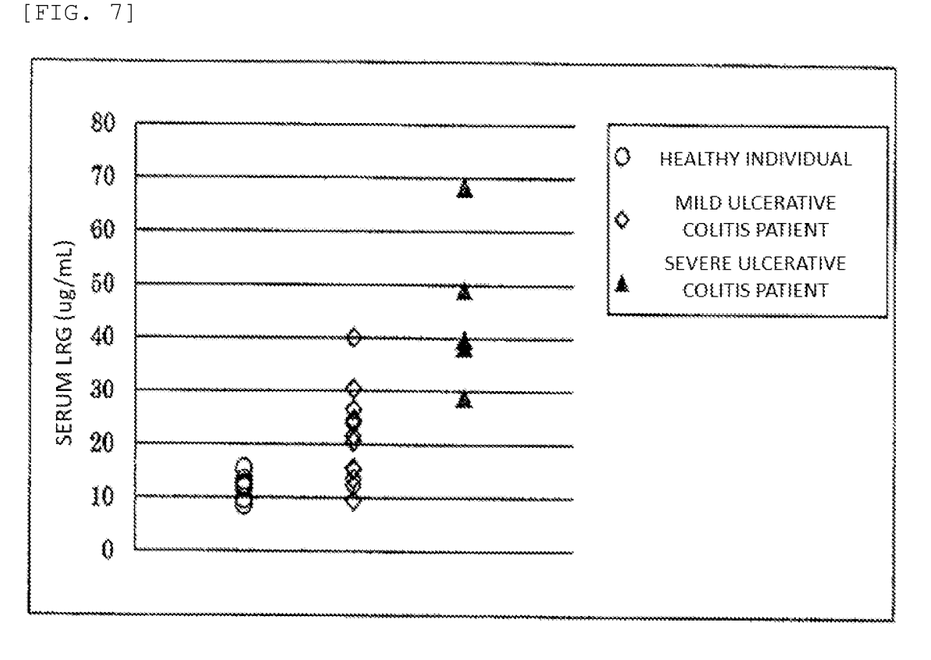
FIG. 7 A graph showing the results of measurement of the LRG concentrations of serum using specimens of healthy individuals and specimens of patients by the measurement method of the invention.

The results are shown in FIG. 7.
According to the results, it was found that LRG in the specimens of healthy individuals and mild and severe ulcerative colitis patients can be measured and that measurement as a marker which can distinguish these states is possible.
Accordingly, the measurement reagent of the invention can play the role of a diagnostic agent.

INDUSTRIAL APPLICABILITY

According to the invention, a measurement method and a measurement reagent for LRG in a biological sample which provide the results easily in a short time could be provided by bringing a biological sample containing LRG and insoluble carrier particles carrying anti-LRG monoclonal antibodies into contact with each other in a liquid phase and measuring the degree of agglutination. The measurement method and the measurement reagent of the invention can be applied also to a general-purpose automated analyzer, and thus easy and simultaneous measurement of a large number of LRG samples has become possible.

Therefore, it has become possible to quantify LRG as a biomarker easily in a short time and easily evaluate the activity of a disease such as inflammatory bowel disease.

The invention claimed is:

1. An immunological measurement method for leucine-rich α2 glycoprotein (LRG) in a biologically derived sample comprising:
   bringing the sample into contact with at least first insoluble carrier particles carrying a first anti-LRG monoclonal antibody and second insoluble carrier particles carrying a second anti-LRG monoclonal antibody in a liquid phase,
   wherein the first and the second insoluble carrier particles are latex particles having average particle sizes of 100 nm to 340 nm, and
   wherein the first and the second insoluble carrier particles are latex particles having critical coagulation concentrations of 65 mM to 270 mM.

2. The measurement method according to claim 1, wherein the average particle size of the first carrier particles carrying the first anti-LRG monoclonal antibody and the average particle size of the second insoluble carrier particles carrying the second anti-LRG monoclonal antibody are the same.

3. The measurement method according to claim 1, wherein the first insoluble carrier particles carrying the first anti-LRG monoclonal antibody and the second insoluble carrier particles carrying the second anti-LRG monoclonal antibody are contained in the same amounts in the liquid phase.

4. The measurement method according to claim 1, wherein the biologically derived sample is serum.

5. The measurement method according to claim 1, wherein the immunological measurement method is an immunoagglutination assay.

6. The measurement method according to claim 5, wherein the immunoagglutination assay is a method based on a homogeneous method.

7. The measurement method according to claim 1, wherein the step of bringing the biologically derived sample into contact with the first insoluble carrier particles carrying the first anti-LRG monoclonal antibody and the second insoluble carrier particles carrying the second anti-LRG monoclonal antibody in the liquid phase comprises the following steps:
   (1) bringing the sample and a first reagent containing a buffer into contact with each other in the liquid phase; and
   (2) adding a second reagent containing the first insoluble carrier particles carrying the first anti-LRG monoclonal antibody and the second insoluble carrier particles carrying the second anti-LRG monoclonal antibody to the liquid phase after step (1).

8. The measurement method according to claim 7, wherein the salt concentration of the liquid phase of (1) is 700 to 900 mM.

9. The measurement method according to claim 1 further comprising:
   optically measuring a degree of agglutination of a complex of LRG, the first insoluble carrier particles carrying the first anti-LRG monoclonal antibody and the second insoluble carrier particles carrying the second anti-LRG monoclonal antibody.

10. The measurement method according to claim 9, wherein the step of optical measuring is a step of measuring an intensity of scattered light, an absorbance or an intensity of transmitted light with an optical device.

11. The measurement method according to claim 1, wherein the latex particles have an average particle size of 150 nm to 260 nm and a critical coagulation concentration of 150 mM to 270 mM.

* * * * *